(12) United States Patent
Shimohirao et al.

(10) Patent No.: US 10,537,506 B2
(45) Date of Patent: Jan. 21, 2020

(54) INCREASING MICRO-ROBUSTNESS

(71) Applicant: Colgate-Palmolive Company, New York, NY (US)

(72) Inventors: Nilza Shimohirao, Sao Paulo (BR); Silvio Santos, Sao Paulo (BR)

(73) Assignee: Colgate-Palmolive Company, New York, NY (US)

( * ) Notice: Subject to any disclaimer, the term of this patent is extended or adjusted under 35 U.S.C. 154(b) by 167 days.

(21) Appl. No.: 15/527,591

(22) PCT Filed: Dec. 1, 2014

(86) PCT No.: PCT/US2014/067888
§ 371 (c)(1),
(2) Date: May 17, 2017

(87) PCT Pub. No.: WO2016/089347
PCT Pub. Date: Jun. 9, 2016

(65) Prior Publication Data
US 2017/0319450 A1 Nov. 9, 2017

(51) Int. Cl.
*A61K 8/34* (2006.01)
*A61Q 11/02* (2006.01)
*A61K 8/30* (2006.01)

(52) U.S. Cl.
CPC .............. *A61K 8/347* (2013.01); *A61Q 11/02* (2013.01); *A61K 8/30* (2013.01)

(58) Field of Classification Search
None
See application file for complete search history.

(56) References Cited

U.S. PATENT DOCUMENTS

| 3,939,260 | A | * | 2/1976 | Lafon | ............ | A61K 8/02 424/401 |
| 4,469,673 | A | | 9/1984 | Iioka et al. | | |
| 5,711,937 | A | | 1/1998 | Nishida et al. | | |
| 6,086,856 | A | | 7/2000 | Saferstein et al. | | |
| 2009/0324515 | A1 | * | 12/2009 | Barra | ............ | A23G 3/36 424/49 |
| 2012/0270183 | A1 | | 10/2012 | Patel et al. | | |

FOREIGN PATENT DOCUMENTS

| EP | 0254452 | | 1/1988 |
| GB | 1166628 | A | 10/1969 |
| JP | H11-246376 | A | 9/1999 |
| JP | H11-322553 | A | 11/1999 |
| JP | 2001-226244 | A | 8/2001 |
| JP | 2002-187829 | A | 7/2002 |
| WO | WO 2011/079075 | | 6/2011 |
| WO | WO 2012/132747 | | 10/2012 |

OTHER PUBLICATIONS

International Search Report and Written Opinion in International Application No. PCT/US2014/067888, dated Jul. 7, 2015.

* cited by examiner

*Primary Examiner* — Nannette Holloman

(57) ABSTRACT

The present invention provides the use of composition a as an antimicrobial agent, wherein the composition comprises anethole, an anionic surfactant, and an orally acceptable vehicle, wherein the composition is free from additional flavor ingredients; and a method of increasing the resistance of a composition to microbial attack, the method comprising formulating the composition so as to comprise anethole, an anionic surfactant, and an orally acceptable vehicle, wherein the composition is free from additional flavor ingredients. The present invention also provides a method of making an oral care composition.

3 Claims, No Drawings

INCREASING MICRO-ROBUSTNESS

BACKGROUND

In many countries, compositions such as oral care compositions are required to comply with certain standards regarding the level of microbes present therein and/or the resistance of the compositions towards microbial attack. In order to ensure that compositions comply with these standards, several initiatives and tools may be implemented throughout the manufacturing process. Resistance of the composition to microbial attack (sometimes termed "micro-robustness") is one of the key elements used to ensure compliance. However, as technology advances, new methods of manufacturing such compositions are introduced. One such technology is the post addition system of manufacturing, in which a partially-complete (i.e. unfinished) composition is prepared and is stored for a certain period of time, after which the remaining ingredients are added in order to form the finished product. The unfinished composition therefore does not contain all the ingredients which are to be included in the finished product, and thus may be more susceptible to microbial attack. Therefore, there is a risk that the unfinished product may become contaminated with microbes, resulting in the finished product having microbial levels which are above the maximum threshold specified by the standards. It would be desirable to increase the resistance to microbial attack of both the finished and unfinished product in such a system of manufacturing.

BRIEF SUMMARY

In one aspect, the present invention provides the use of a composition as an antimicrobial agent wherein the composition comprises anethole, an anionic surfactant, and an orally acceptable vehicle, and wherein the composition is free from additional flavor ingredients.

Optionally, the anionic surfactant is sodium lauryl sulfate.

Optionally, the ratio by weight of anethole to anionic surfactant is from 1:1 to 1:10. Further optionally, the ratio by weight of anethole to anionic surfactant is about 1:5.

Optionally, the compositions a partially-complete oral care composition produced during a post addition system method of manufacture.

Optionally, the anethole is present in the composition in an amount of from 0.01 to 0.5 weight %, based on the weight of the composition. Further optionally, the anethole is present in the composition in an amount of from 0.05 to 0.25 weight %, based on the weight of the composition. Still further optionally, the anethole is present in the composition in an amount of about 0.08 weight %, based on the weight of the composition.

Optionally, the anionic surfactant is present in the composition in an amount of from 0.05 to 1 weight %, based on the weight of the composition. Further optionally, the anionic surfactant is present in the composition in an amount of from 0.1 to 0.75 weight %, based on the weight of the composition. Still further optionally, the anionic surfactant is present in the composition in an amount of about 0.4 weight %, based on the weight of the composition.

In a second aspect, the present invention provides a method of increasing the resistance of a composition to microbial attack, the method comprising formulating the composition so as to contain anethole, an anionic surfactant, and an orally acceptable vehicle, wherein the composition is free from additional flavor ingredients.

Optionally, the anionic surfactant is sodium lauryl sulfate.

Optionally, the ratio by weight of anethole to anionic surfactant in the composition is from 1:1 to 1:10. Further optionally, the ratio by weight of anethole to anionic surfactant in the composition is about 1:5.

Optionally, the composition is a partially-complete oral care composition produced during a post addition system method of manufacture.

Optionally, the anethole is present in the composition in an amount of from 0.01 to 0.5 weight %, based on the weight of the composition. Further optionally, the anethole is present in the composition in an amount of from 0.05 to 0.25 weight %, based on the weight of the composition. Still further optionally, the anethole is present in the composition in an amount of about 0.08 weight %, based on the weight of the composition.

Optionally, the anionic surfactant is present in the composition in an amount of from 0.05 to 1 weight %, based on the weight of the composition. Further optionally, the anionic surfactant is present in the composition in an amount of from 0.1 to 0.75 weight %, based on the weight of the composition. Still further optionally, the anionic surfactant is present in the composition in an amount of about 0.4 weight %, based on the weight of the composition.

In a third aspect, the present invention provides a method of making an oral care composition, the method comprising: (a) preparing a first composition which comprises anethole, an anionic surfactant, and an orally acceptable vehicle, wherein the composition is free from additional flavor ingredients; and (b) storing the first composition for a period of up to 48 hours.

Optionally, the additional flavor ingredients comprise menthol, menthyl lactate, menthyl acetate, spearmint oil, peppermint oil, clove oil, parsley oil, cinnamon oil, oil of wintergreen, bay oil, anise oil, eucalyptus oil, sage, marjoram, vanillin, citrus oils, fruit oils, fruit essences, nut oils and nut essences.

Optionally, following step (b), the method further comprises the step of: (c) adding at least one additional flavor ingredient to the first composition.

Optionally, the at least one additional flavor ingredient is selected from menthol, menthyl lactate, menthyl acetate, spearmint oil, peppermint oil, clove oil, parsley oil, cinnamon oil, oil of wintergreen, bay oil, anise oil, eucalyptus oil, sage, marjoram, vanillin, citrus oils, fruit oils, fruit essences, nut oils and nut essences.

Optionally, the first composition further comprises at least one ingredient selected from humectants, diluents, abrasives, sweeteners, fluoride ion sources, and thickeners.

Optionally, the first composition comprises at least one ingredient selected from precipitated calcium carbonate, sorbitol, sodium fluoride, sodium saccharin, carboxymethylcellulose and water. Further optionally, the first composition comprises precipitated calcium carbonate, sorbitol, sodium fluoride, sodium saccharin, carboxymethylcellulose and water.

Optionally, the anionic surfactant is sodium lauryl sulfate.

Optionally, the ratio by weight of anethole to anionic surfactant is from 1:1 to 1:10. Further optionally, the ratio by weight of anethole to anionic surfactant is about 1:5.

Optionally, the anethole is present in the first composition in an amount of from 0.01 to 0.5 weight %, based on the weight of the first composition. Further optionally, the anethole is present in the first composition in an amount of from 0.05 to 0.25 weight %, based on the weight of the first composition. Still further optionally, the anethole is present in the first composition in an amount of about 0.08 weight %, based on the weight of the first composition.

Optionally, the anionic surfactant is present in the first composition in an amount of from 0.05 to 1 weight %, based on the weight of the first composition. Further optionally, the anionic surfactant is present in the first composition in an amount of from 0.1 to 0.75 weight %, based on the weight of the first composition. Still further optionally, the anionic surfactant is present in the first composition in at mount of about 0.4 weight %, based on the weight of the first composition.

Further areas of applicability of the present invention will become apparent from the detailed description provided hereinafter. It should be understood that the detailed description and specific examples, while indicating the preferred embodiment of the invention, are intended for purposes of illustration only and are not intended to limit the scope of the invention.

DETAILED DESCRIPTION

The following description of the preferred embodiment(s) is merely exemplary in nature and is in no way intended to limit the invention, its application, or uses.

As used throughout, ranges are used as shorthand for describing each and every value that is within the range. Any value within the range can be selected as the terminus of the range. In addition, all references cited herein are hereby incorporated by referenced in their entireties. In the event of a conflict in a definition in the present disclosure and that of a cited reference, the present disclosure controls.

Unless otherwise specified, all percentages and amounts expressed herein and elsewhere in the specification should be understood to refer to percentages by weight. The amounts given are based on the active weight of the material.

Unless otherwise specified, all ratios expressed herein should be understood to refer to ratios by weight.

The present inventors have surprisingly found that the inclusion of a combination of anethole and an anionic surfactant (such as sodium lauryl sulfate) in a composition increases its micro-robustness (i.e. resistance to microbial attack). When the composition is a partially-complete composition produced during a post addition system method of manufacture, this increase in micro-robustness allows for the partially-complete composition to be stored for a longer period of time before adding the remaining ingredients to form the finished product, whilst still fulfilling the standards required of such products regarding the level of microbes present.

In a first aspect, therefore, the present invention provides the use of a combination of anethole and an anionic surfactant as an antimicrobial agent.

In a second aspect, the present invention provides a method of increasing the resistance of a composition to microbial attack, the method comprising formulating the composition so as to contain anethole and an anionic surfactant.

Examples of anionic surfactants which may be used in accordance with the above use and method of the present invention include water-soluble salts of $C_{8-20}$ alkyl sulfates, sulfonated monoglycerides of $C_{8-20}$ fatty acids, sarcosinates, taurates and the like. Illustrative examples of these and other classes include sodium lauryl sulfate (SLS), sodium coconut monoglyceride sulfonate, sodium laurel sarcosinate, sodium lauryl isoethionate, sodium laureth carboxylate and sodium dodecyl benzenesulfonate. In some embodiments, the anionic surfactant is sodium lauryl sulfate.

In any embodiments of either of the above aspects, the ratio by weight of anethole to anionic surfactant may be from 1:1 to 1:10, from 1:2 to 1:9, from 1:3 to 1:8 from 1:4 to 1:7, from 1:4 to 1:6, or about 1:5.

In any embodiments of either of the above aspects, the anethole and the anionic surfactant may be present in a composition which comprises an orally-acceptable or topically-acceptable vehicle. In some such embodiments, the composition is an oral care composition comprising an orally-acceptable vehicle. The oral care composition may be a dentifrice, a dental cream, a toothpaste, a tooth gel, a mouthwash, a mouthrinse, a gum, or a film; particularly a dental cream, a toothpaste or a tooth gel. In other such embodiments, the composition comprises an orally-acceptable vehicle, and is a partially-complete oral care composition produced during a post addition system method of manufacture. In other embodiments, the composition is a personal care composition comprising a topically-acceptable vehicle. In some such embodiments, the composition comprises a topically-acceptable vehicle, and is a partially-complete personal care composition produced during a post addition system method of manufacture.

By a "a post addition system method of manufacture" is meant a method in which a partially-complete composition (i.e. an unfinished composition which does not include all of the ingredients which are to be present in the finished product) is prepared and is stored for a certain period of time, after which period of time the remaining ingredients are then added in order to form the finished product.

Ingredients which may be present in the partially-complete composition include humectants (such as sorbitol, xylitol or glycerin), diluents (such as water), abrasives (such as precipitated calcium carbonate (PCC), natural calcium carbonate (NCC) or silica abrasives), sweeteners (such as sodium saccharin), fluoride ion sources (such as sodium fluoride), and thickeners (e.g. cellulose polymers such as carboxymethylcellulose). In some embodiments, the partially-complete composition contains at least one ingredient selected from precipitated calcium carbonate, sorbitol, sodium fluoride, sodium saccharin, carboxymethylcellulose and water. In certain embodiments, the partially-complete composition comprises precipitated calcium carbonate, sorbitol, sodium fluoride, sodium saccharin, carboxymethylcellulose and water.

The partially-complete composition is free from additional flavor ingredients. As used herein, the term "additional flavor ingredients" means flavor ingredients other than anethole. At least one such additional flavor ingredient may be added to the partially-complete composition after it has been stored for a certain period of time in order to form the finished product. This period of time may be up to 48 hours. Examples of additional flavor ingredients include, but are not limited to: menthol and its derivatives (such as menthyl lactate or menthyl acetate), spearmint oil, peppermint oil, clove oil, parsley oil cinnamon oil, oil of wintergreen, bay oil anise oil, eucalyptus oil, sage, marjoram, vanillin, citrus oils, fruit oils, fruit essences, nut oils and nut essences. The combination of the at least one additional flavor ingredient and the anethole constitutes the flavor formula of the finished product.

In any embodiments of either of the above aspects, the anethole may be present in the composition in an amount of from 0.01 to 0.5 weight %, from 0.02 to 0.4 weight %, from 0.03 to 0.3 weight %, from 0.05 to 0.25 weight %, from 0.06 to 0.15 weight %, from 0.07 to 0.1 weight %, or about 0.08 weight %, based on the weight of the composition.

In any embodiments of either of the above aspects, the anionic surfactant may be present in the composition in an amount of from 0.05 to 1 weight %, from 0.075 to 0.9 weight %, from 0.1 to 0.75 weight %, from 0.2 to 0.6 weight %, from 0.3 to 0.5 weight %, or about 0.4 weight %, based on the weight of the composition.

In a third aspect, the present invention provides a method of making an oral care composition, the method comprising: (a) preparing a first composition which comprises anethole, an anionic surfactant, and an orally acceptable vehicle, wherein the composition is free from additional flavor ingredients; and (b) storing the first composition for a period of up to 48 hours.

The present inventors have surprisingly found that, when anethole and an anionic surfactant are included in the first composition (partially-complete composition in a post addition system method of manufacture), this first composition can be stored for 48 hours while still meeting the relevant standards concerning the level of microbes present therein and/or its resistance towards microbial attack. This represents an improvement upon partially-complete compositions which do not contain anethole and an anionic surfactant, which can only be stored for a maximum of 24 hours (ideally no more than 6 hours) due to their lack of micro-robustness.

In some embodiments, the additional flavor ingredients comprise menthol, menthyl lactate, menthyl acetate, spearmint oil, peppermint oil, clove oil, parsley oil, cinnamon oil, oil of wintergreen, bay oil, anise oil, eucalyptus oil, sage, marjoram, vanillin, citrus oils, fruit oils, fruit essences, nut oils and nut essences.

In some embodiments, following step (b), the method further comprises the step of: (c) adding at least one additional flavor ingredient to the first composition.

In some embodiments, the at least one additional flavor ingredient is selected from menthol, menthyl lactate, menthyl acetate, spearmint oil peppermint oil, clove oil, parsley oil, cinnamon oil, oil of wintergreen, bay oil, anise oil, eucalyptus oil, sage, marjoram, vanillin, citrus oils, fruit oils, fruit essences, nut oils and nut essences.

In some embodiments, the first composition further comprises at least one ingredient selected from humectants (such as sorbitol, xylitol or glycerin), diluents (such as water), abrasives (such as precipitated calcium carbonate (PCC), natural calcium carbonate (NCC) or silica abrasives), sweeteners (such as sodium saccharin), fluoride ion sources (such as sodium fluoride), and thickeners (e.g. cellulose polymers such as carboxymethylcellulose). In some embodiments, the partially-complete composition contains at least one ingredient selected from precipitated calcium carbonate, sorbitol, sodium fluoride, sodium saccharin, carboxymethylcellulose and water. In certain embodiments, the partially-complete composition comprises precipitated calcium carbonate, sorbitol, sodium fluoride, sodium saccharin, carboxymethylcellulose and water.

Examples of anionic surfactants which may be used in accordance with the above method of making an oral care composition include water-soluble salts of $C_{8-20}$ alkyl sulfates, sulfonated monoglycerides of $C_{8-20}$ fatty acids, sarcosinates, taurates and the like. Illustrative examples of these and other classes include sodium lauryl sulfate (SLS) sodium coconut monoglyceride sulfonate, sodium lauryl sarcosinate, sodium lauryl isoethionate, sodium laureth carboxylate and sodium dodecyl benzenesulfonate. In some embodiments, the anionic surfactant is sodium lauryl sulfate.

In some embodiments, the ratio by weight of anethole to anionic surfactant may be from 1:1 to 1:10, from 1:2 to 1:9, from 1:3 to 1:8, from 1:4 to 1:7, from 1:4 to 1:6, or about 1:5.

In some embodiments, the anethole may be present in the first composition in an amount of from 0.01 to 0.5 weight %, from 0.02 to 0.4 weight %, from 0.03 to 0.3 weight %, from 0.05 to 0.25 weight %, from 0.06 to 0.15 weight %, from 0.07 to 0.1 weight %, or about 0.08 weight %, based on the weight of the first composition.

In some embodiments, the anionic surfactant may be present in the first composition in an amount of from 0.05 to 1 weight %, from 0.075 to 0.9 weight %, from 0.1 to 0.75 weight %, from 0.2 to 0.6 weight %, from 0.3 to 0.5 weight %, or about 0.4 weight %, based on the weight of the first composition.

In any embodiments of the first, second and third aspect of the present invention which relate to oral care compositions, the oral care compositions may further comprise additional ingredients. These additional ingredients may include, but are not limited to, diluents (e.g. water), bicarbonate salts, pH modifying agents, non-ionic or amphoteric surfactants, foam modulators, thickening agents, humectants, sweeteners, colorants, antibacterial agents, anticaries agents, and mixtures thereof. The orally-acceptable vehicle of the compositions may include diluents, humectants, foam modulators, thickening agents, sweeteners, fluoride ion sources, abrasives or mixtures thereof.

The oral care compositions may also comprise at least one amphoteric (e.g. betaine) or nonionic surfactant, which may be present in a total amount of about 0.01 wt. % to about 10 wt. %, for example, from about 0.05 wt. % to about 5 wt. %, or from about 0.1 wt % to about 2 wt. % by total weight of the oral care composition.

The oral care compositions may comprise at least one foam modulator, useful for example to increase amount, thickness or stability of foam generated by the composition upon agitation. One or more foam modulators are optionally present in a total amount of about 0.1 wt. % to about 10 wt. %, for example from about 0.2 wt. % to about 5 wt. %, or from about 0.25 wt. % to about 2 wt. %, by total weight of the oral care composition.

The oral care compositions may comprise at least one sweetener, useful for example to enhance taste of the composition. One or more sweeteners are optionally present in a total amount depending strongly on the particular sweeteners) selected, but typically 0.005 wt. % to 5 wt. %, by total weight of the composition, optionally 0.01 wt. % to 1 wt. %, further optionally 0.1 wt. % to 0.5 wt. % by total weight of the oral care composition.

The oral care compositions may comprise at least one colorant. Colorants herein include pigments, dyes, lakes and agents imparting a particular luster or reflectivity such as pearling agents. Any orally acceptable colorant can be used. One or more colorants are optionally present in a total amount of from about 0.0001 wt. % to about 5 wt. %, for example, from about 0.0001 wt. %, to about 1 wt. %, or from about 0.0005 wt. % to about 0.1 wt. %, by total weight of the oral care composition.

The oral care compositions may comprise a fluoride ion source. Fluoride ion sources may be added to the oral care compositions at a level of about 0.001 wt. % to about 10 wt. %, e.g., from about 0.003 wt. % to about 5 wt. %, 0.01 wt. % to about 1 wt., or about 0.05 wt. %. However, it is to be understood that the weights of fluoride salts to provide the appropriate level of fluoride ion will obviously vary based on the weight of the counter ion in the salt, and one of skill in the art may readily determine such amounts. The amount of fluoride ion source present may also vary depending on country specific regulations.

The oral care compositions may comprise a saliva stimulating agent useful, for example, in amelioration of dry mouth. One or more saliva stimulating agents are optionally present in saliva stimulating effective total amount.

The oral care compositions may include antisensitivity agents. Such agents may be added in effective amounts, e.g., from about 1 wt. % to about 20 wt. % by weight based on the total weight of the oral care composition, depending on the agent chosen.

The oral care composition of the invention may further comprise an antioxidant.

EXAMPLES

Example 1

A micro-robustness test was developed to measure the resistance of the compositions to microbial attack. The micro-robustness test is a quantitative measure (arising from the area under the curve (AUC), in a plot of bacterial count (y-axis) against time (x-axis)—see the calculation below) of the sample's ability to withstand microbial insult. The resistance of the compositions to microbial attack was quantified in terms of their Micro-Robustness Index (MRI), as discussed below.

The composition under test was diluted in culture media (broth base) and then added to inoculum to form the test material. At selected time intervals, the test material and the control (inoculum with no test composition present) were sampled. Dilutions and plating were performed to recover the surviving organisms, and bacterial counts (in terms of colony forming units, CFU) were carried out for both the test material and the control. The log difference in the bacterial counts between the test material and the inoculum control was calculated at these different time intervals. The calculation is done as follows:
1. Convert CFU to Log CFU
2. Calculate log reduction at each time point for the test material versus the control (at 4, 6, and 24 hours), i.e. "log reduction"–log ($CFU_{test\ material}$)–log ($CFU_{control}$)
3. Calculate the area under the curve (AUC) for a plot of log reduction against time
4. The AUC value for the test material is compared with the AUC value obtained (by the method above) for the category standard formulation (which contains methyl paraben and propyl paraben as preservatives, and also contains anethole as part of its flavor formula), by dividing the test material AUC value by the category standard AUC value. The resulting number is the Micro Robustness Index (MRI).

The minimum MRI required in order for a composition to be considered sufficiently micro-robust is 0.75.

Two dental cream bases were tested, which differed only in that Dental Cream Base 1 contained 0.08 weight % anethole and 0.4 weight % sodium lauryl sulfate, whereas Dental Cream Base 2 contained no anethole and no sodium lauryl sulfate. Neither of the two dental cream bases contained any other antimicrobial agents. The Micro-Robustness Index for the two dental creams is shown in Table 1, below:

TABLE 1

| Dental Cream Base | MRI |
|---|---|
| #1 (0.08 weight % anethole/0.4 weight % SLS) | 1.05 |
| #2 | 0.20 |

As can be seen from the data in Table 1, above, the addition of 0.08 weight % anethole and 0.4 weight % sodium lauryl sulfate to the dental cream base resulted in an increase in the Micro-Robustness Index from 0.20 to 1.05. The presence of the anethole/sodium lauryl sulfate combination thus results in an increase in resistance of the composition towards microbial attack, and ensures compliance with the required standards for such compositions.

What is claimed is:

1. A method of increasing the resistance of an oral care composition to microbial attack during a post-addition system of manufacture, the method comprising
   formulating a partially-complete composition comprising anethole, sodium lauryl sulfate (SLS), and an orally acceptable vehicle, wherein the partially-complete composition is free from additional flavor ingredients;
   wherein the amount of anethole in the partially-complete composition is from 0.05-0.25 weight %, based on the weight of the partially-complete composition; and
   wherein the sodium lauryl sulfate is present in the partially-complete composition in an amount of from 0.1 to 0.75 weight %, based on the weight of the composition;
   storing the partially-complete composition for up to 48 hours, then
   adding additional ingredients, including at least one additional flavor ingredient, to the partially-complete composition to form a completed oral care composition.

2. The method of claim 1, wherein the ratio by weight of anethole to SLS in the composition is from 1:1 to 1:10.

3. The method of claim 2, wherein the ratio by weight of anethole to SLS in the composition is about 1:5.

* * * * *